(12) United States Patent
Sonnenschein

(10) Patent No.: US 10,631,833 B2
(45) Date of Patent: Apr. 28, 2020

(54) REMOTELY CONTROLLED ULTRASOUND TRANSDUCER

(71) Applicant: PULSENMORE LTD., Tel Aviv-Jaffa (IL)

(72) Inventor: Lazar Sonnenschein, Omer (IL)

(73) Assignee: PULSENMORE LTD., Tel Aviv-Jaffa (IL)

( * ) Notice: Subject to any disclaimer, the term of this patent is extended or adjusted under 35 U.S.C. 154(b) by 323 days.

(21) Appl. No.: 15/557,527

(22) PCT Filed: Mar. 21, 2016

(86) PCT No.: PCT/IL2016/050302
§ 371 (c)(1),
(2) Date: Sep. 12, 2017

(87) PCT Pub. No.: WO2016/151577
PCT Pub. Date: Sep. 29, 2016

(65) Prior Publication Data
US 2018/0042581 A1     Feb. 15, 2018

(30) Foreign Application Priority Data
Mar. 26, 2015 (IL) .......................................... 237980

(51) Int. Cl.
*A61B 8/00* (2006.01)
(52) U.S. Cl.
CPC .............. *A61B 8/56* (2013.01); *A61B 8/4411* (2013.01); *A61B 8/4427* (2013.01);
(Continued)

(58) Field of Classification Search
CPC ... A61B 8/4494; A61B 8/4411; A61B 8/4427; A61B 8/4461; A61B 8/56; A61B 8/4472;
(Continued)

(56) References Cited

U.S. PATENT DOCUMENTS

2008/0269606 A1\* 10/2008 Matsumura .......... A61B 5/0048
600/438
2009/0043204 A1    2/2009 Pelissier et al.
(Continued)

FOREIGN PATENT DOCUMENTS

IL           236484         6/2016
JP       H06327681 A       11/1994
(Continued)

OTHER PUBLICATIONS

International Preliminary Report on Patentability for PCT/IL2016/050302, 10 pages, dated Feb. 12, 2017.
(Continued)

*Primary Examiner* — Bo Joseph Peng
(74) *Attorney, Agent, or Firm* — Roach Brown McCarthy & Gruber, P.C; Kevin D. McCarthy

(57) ABSTRACT

A base for an ultrasonic system comprises elements adapted to connect either a smart device or a display device to the base such that the base and smart device can be moved as a single unit. The base also comprises an ultrasonic array with at least one element capable of generating a signal in the range of 1 MHz to 15 MHz and a gimbal system configured to allow the ultrasonic array to be tilted relative to the base. The base provides a way for a physician to remotely control the transmitting angle and pressure exerted against the skin of an ultrasound transducer array of an ultrasound scanning system that is handheld by a patient.

21 Claims, 7 Drawing Sheets

(52) U.S. Cl.
CPC .......... *A61B 8/4461* (2013.01); *A61B 8/4466* (2013.01); *A61B 8/4472* (2013.01); *A61B 8/4494* (2013.01); *A61B 8/461* (2013.01); *A61B 8/469* (2013.01); *A61B 8/565* (2013.01)

(58) Field of Classification Search
CPC ......... A61B 8/461; A61B 8/469; A61B 8/565; A61B 8/4466
See application file for complete search history.

(56) References Cited

U.S. PATENT DOCUMENTS

| | | |
|---|---|---|
| 2009/0198132 A1 | 8/2009 | Pelissier et al. |
| 2010/0016744 A1 | 1/2010 | Brost et al. |
| 2012/0289833 A1 | 11/2012 | Kashima et al. |
| 2015/0038844 A1 | 2/2015 | Blalock et al. |

FOREIGN PATENT DOCUMENTS

| | | |
|---|---|---|
| JP | 2004-041594 A | 2/2004 |
| JP | 2012-254279 A | 12/2012 |
| JP | 2014-150936 A | 8/2014 |
| WO | 2014133665 A1 | 9/2014 |

OTHER PUBLICATIONS

International Search Report for PCT/IL2016/050302, 3 pages, dated Jun. 21, 2016.
Written Opinion of the International Searching Authority for PCT/IL2016/050302, 6 pages, dated Jun. 21, 2016.
Communication and Supplementary European Search Report for a counterpart foreign application—EP 16 76 7869—dated Nov. 7, 2018; 7 pages.
An office action from the Japanese patent office in a counterpart foreign application—2017-550120, dated Mar. 13, 2020—3 pages—and an English machine translation thereof—3 pages.

\* cited by examiner

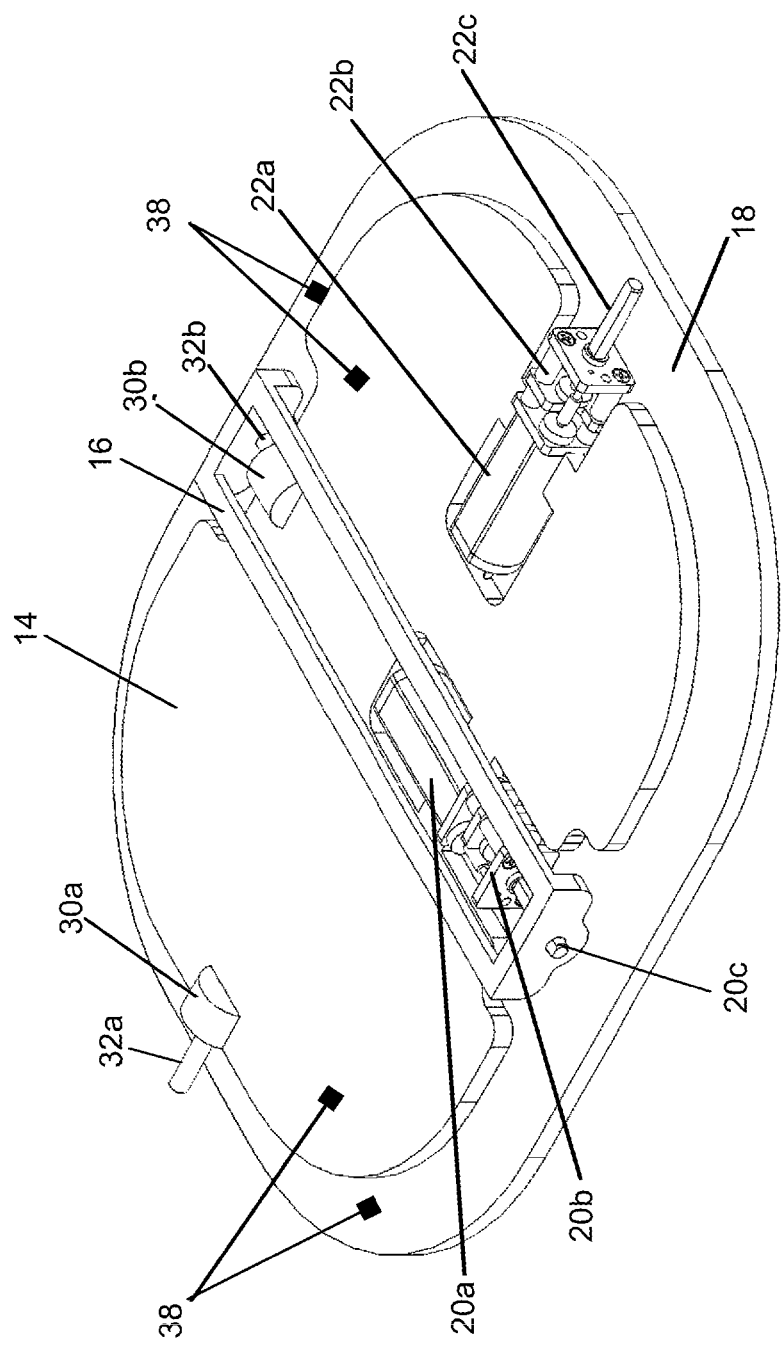
Fig. 4B
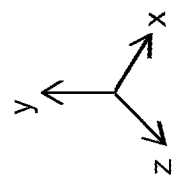

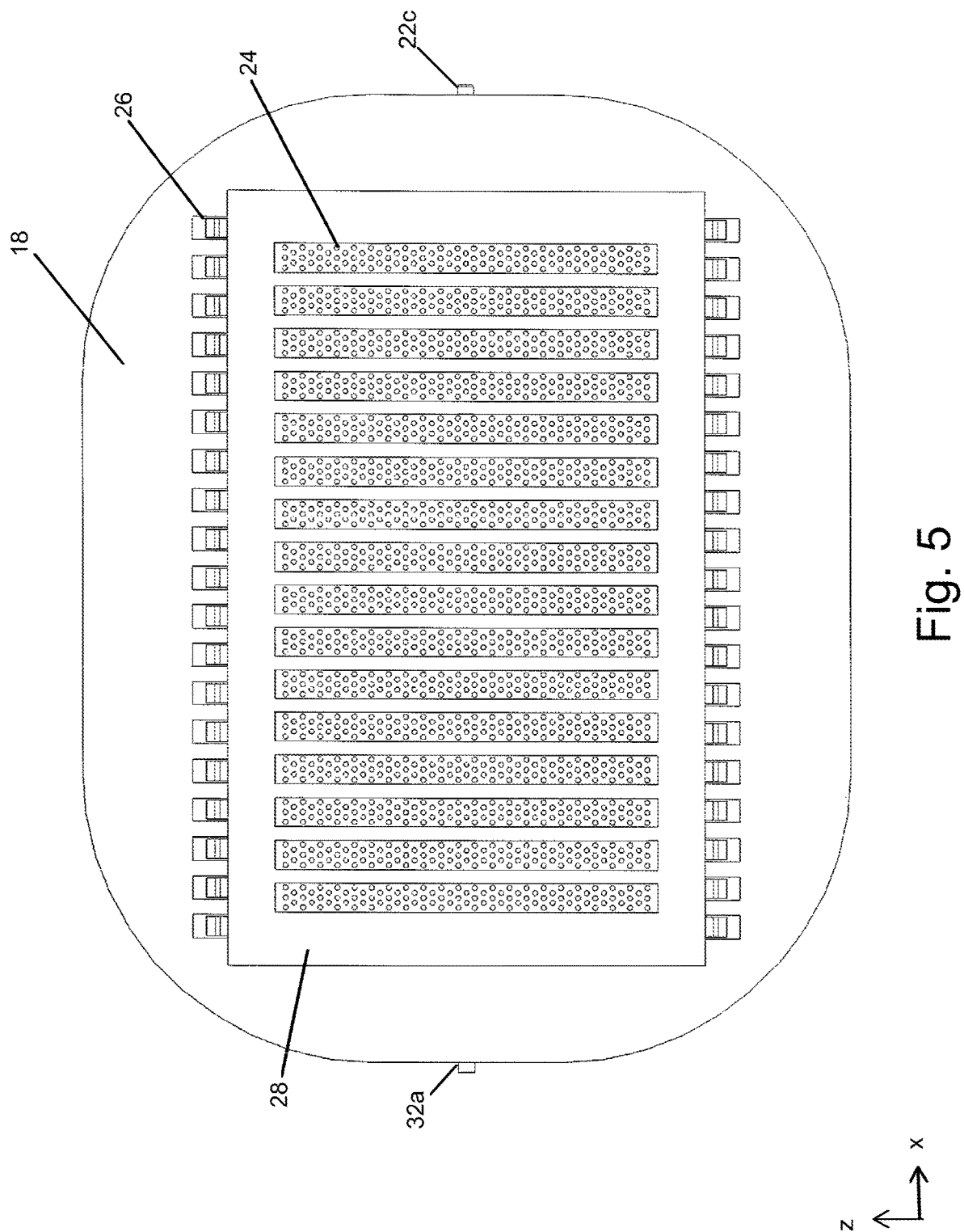

REMOTELY CONTROLLED ULTRASOUND TRANSDUCER

FIELD OF THE INVENTION

The present invention relates to the field of medical devices. In particular, the invention relates to the field of devices and systems for monitoring of internal organs of humans and animals and therapy combined with ultrasound.

BACKGROUND OF THE INVENTION

The applicant of this application has described in co-pending Israeli Patent Application IL 236484 a handheld ultrasound scanning system that can be owned and operated by private untrained individuals as well as by doctors and trained medical personnel and healthcare givers.

The system comprises a base that functions as a docking station for a smart device. The base comprises a socket into which the smart device can be inserted on its top side and ultrasound transducer elements, which are essentially integral with additional electronics, located on its bottom side as will be more fully described herein below. The base is provided with connecting elements suitable to connect it to the smart device.

When it is desired to perform an ultrasound scan, for example to monitor the activity of a fetus, the smart phone is turned on and an ultrasound software application is launched from the base or from the smart device or, in some embodiments part of the software resides on the base and part on the smart device. In other embodiments the application is downloaded from the cloud or transmitted from a communication station such as that of a mobile services provider or a satellite.

The base is now moved along the pregnant woman's abdomen and images or video generated by the ultrasound system are stored in a memory in the base or in the smart device for viewing and/or transmitting to a physician or hospital, as the case may be. In embodiments of the invention communication to and from the system can be via a unique IP address assigned to the base or by using the mobile number of the smart device. Therefore the physician, for example, can contact the base via any IP communication, using a communication channel (secured or unsecured) in order to send voice instructions to be heard by the patient for example, or to see the patient via camera in the device, or to instruct the patient to move the base in a certain direction in order to acquire images at different positions, or the physician can send still images or video movies from the base or the patient's smart device to a device controlled by him, such as, for instance, to a PC or a mobile device.

An exemplary embodiment of a base according to IL236484 is shown in FIG. 1, and is generally indicated by arrow 100. The base, in this embodiment, is provided with a cavity 101, which is suitable to house a smart device of given dimensions. This cavity, however, can, in other embodiments, be replaced by any other connection and positioning elements, suitable to keep the smart device and the base conveniently, reversibly, physically connected to allow said base and said smart device to be moved as a single unit, for example, the base can be provided with an enclosure to house the entire smart device. In the exemplary embodiment of FIG. 1, a socket 102 is provided in the lower part of the base, in which a connector (not shown) is located. The connector can be configured to electrically connect electronics of an ultrasound array located on the base. The connector can be, for instance, a USB connector such as used by an Apple iPhone, Samsung Galaxy, Sony Experia, etc., or a different type of connector as used by other phones such as Huawei, Nokia, etc. or other connectors on smart devices, e.g. an audio jack or a Mobile Industry Processor Interface (MIPI) that can provide at least transfer of 10 images per a second or at a minimum 10 VGA resolution images per a second. The connector can also be used as mechanical alignment device.

Turning now to FIG. 2, the bottom portion of the device 100 of FIG. 1 is seen. On the bottom outer surface of device 100 is located an ultrasound transducer 103. Embodiments of the ultrasound transducer 103 as well as the electronics that operates the ultrasound system, which are located between ultrasound transducer 103 and the connector in socket 102 or in the smart device itself, are described in IL236484.

FIG. 3A shows a smart device 301, in this example a smartphone, fitted into the cavity in base 300. The connector in the socket at the bottom of the cavity may provide the electrical connection between the electronics in base 300 and smartphone 301 and/or the alignment between the smart device and the base. It is possible to exchange data, for example, patient number, time, medical records, etc. between the smart device and the socket. Additionally, the connector and the sides of the cavity connect the smart device mechanically to the base so that they can be moved together across a surface, e.g. a human's abdomen or chest, as a single unit.

The ultrasound transducer 103 described above could be replaced in all cases by suitable elements that are excited and generate pressure waves, such as single elements, an array of elements, a linear array, a focused array, a multi-dimensional array, i.e., a 1.5D, 2D and 3D array. The elements may be straight or curved with different shapes and can be constructed on a plane, a convex, or a concave surface. The transducer elements can be made from different materials such as, for example, Piezo, Piezo composite, and arrays made with known techniques on silicon based substrates, for example, CMUT (Capacitive micromachined ultrasonic transducers), PMUT (Piezoelectric Micromachined Ultrasonic Transducers), MEMS (Microelectromechanical systems), and NEMS (Nanoelectromechanical systems) and elements directly connected to the smart device.

The ultrasound system in IL236484 can be adapted to include any type of "smart device". Examples of "smart devices" include smartphones, tablets, and micro and mini computers; however the term "smart device" should be interpreted in the broadest way to include each and every device that has the capacity to receive an input, to run software and, optionally, is provided with communication capabilities, such as Wi-Fi, WI-GIG, LTE, S-UMTS, HSPA+, advanced wireless communication, wired communication, mobile communication generation such as 4G, 4.5G, 5G, 6G, Bluetooth, cellular networks, and with any communication protocol that connects two independent devices.

As said above, in embodiments of the system the physician can contact the base via IP communication to send a message or voice instructions to be heard by the patient for example, to instruct the patient to move the base in a certain direction in order to acquire images at different positions or to instruct via a camera that is an integral part of the smartphone. While this arrangement is adequate to provide the physician with the images that he requires in many application, e.g. fetal monitoring, in other applications, e.g. cardiac monitoring, or lung monitoring, much finer control over the angle at which the ultrasound waves are directed towards the organ to be studied and also of the pressure and orientation with which the transducer is pressed against the patient's skin are crucial to the physician's ability to obtain useful information from the images. Such fine control is difficult to achieve using voice instructions from physician to patient.

It is therefore a purpose of the present invention to provide a way for a physician to remotely control the transmitting angle and pressure exerted against the skin of an ultrasound transducer array of an ultrasound scanning system that is handheld by a patient.

Further purposes and advantages of this invention will appear as the description proceeds.

SUMMARY OF THE INVENTION

In a first aspect the invention is a base for an ultrasonic system. The base comprises: elements adapted to connect one of a smart device or a display device to the base such that the base and smart device can be moved as a single unit, an ultrasonic array with at least one element capable of generating a signal having frequency in the range between 1 MHz to 15 MHz, and a system configured to allow the ultrasonic array to be tilted relative to the base.

To illustrate the system configured to allow the ultrasonic array to be tilted relative to the base, a specific design of gimbal system is described herein but skilled persons will be able to device other arrangements that can be used to accomplish the goals of the invention. The exemplary gimbal system comprises a gimbal support rigidly connected to the inside of the base, an inner gimbal ring rotatably attached to the gimbal support and an outer gimbal ring rotatably attached to the inner gimbal ring. The ultrasonic array is attached to a PCB that is fixedly attached to the outer gimbal ring. Rotation of each of the inner gimbal ring and the outer gimbal ring is caused by a separate motor and micro-gear assembly.

In embodiments of the base of the first aspect of the invention the motors of the gimbal system are activated and controlled from a remote location.

In embodiments of the base of the first aspect of the invention the motors of the gimbal system are activated and controlled by a remotely located real or virtual joystick or by keys on a real or virtual keyboard.

In embodiments of the base of the first aspect of the invention the motors of the gimbal system are chosen from: electric motors, magnetic motors, and piezo motors.

Embodiments of the base of the first aspect of the invention comprise at least one three dimensional accelerometer on at least one of the base, the ultrasound array PCB, the inner gimbal ring, and the outer gimbal ring.

Embodiments of the base of the first aspect of the invention comprise at least one pressure sensor located on at least one of the base and the ultrasound array.

In a second aspect the invention is a system for ultrasonic imaging comprising: a base according to the first aspect of the invention and either a smart device or a display device.

In embodiments of the system of the invention the gimbal system comprises a gimbal support rigidly connected to the inside of the base, an inner gimbal ring rotatably attached to the gimbal support and an outer gimbal ring rotatably attached to the inner gimbal ring and the ultrasonic array is attached to a PCB that is fixedly attached to the outer gimbal ring.

In embodiments of the system of the invention rotation of each of the inner gimbal ring and the outer gimbal ring is caused by a separate motor and micro-gear assembly.

In embodiments of the system of the invention the motors of the gimbal system are activated and controlled from a remote location. In embodiments of the system of the invention the motors of the gimbal system are activated and controlled by a remotely located real or virtual joystick or by keys on a real or virtual keyboard.

In embodiments of the system of the invention the motors of the gimbal system are chosen from: electric motors, magnetic motors and piezo motors.

Embodiments of the system of the invention comprise at least one 3 dimensional accelerometer on at least one of the base, the ultrasound array PCB, the inner gimbal ring, and the outer gimbal ring.

Embodiments of the system of the invention comprise at least one pressure sensor located on at least one of the base and the ultrasound array.

In a third aspect the invention is a base for an ultrasonic system. The base comprises: elements adapted to connect a smart device to the base such that the base and smart device can be moved as a single unit, an ultrasonic array with at least one element capable of generating a signal having a frequency in the range between 1 MHz to 15 MHz, and a gimbal system connected to the inside of the base. The gimbal system comprises: an inner gimbal ring rotatably attached to the gimbal support and an outer gimbal ring rotatably attached to the inner gimbal ring. The ultrasonic array is attached to a PCB that is fixedly attached to the outer gimbal ring and the gimbal system is configured to tilt the ultrasonic array relative to the base.

In a fourth aspect the invention is a base for an ultrasonic system. The base comprises: elements adapted to connect a smart device to the base such that the base and smart device can be moved as a single unit, an ultrasonic array with at least one element capable of generating a signal having a frequency in the range between 1 MHz to 15 MHz, and a gimbal system comprised of a gimbal support rigidly connected to the inside of the base, an inner gimbal ring rotatably attached to the gimbal support and an outer gimbal ring rotatably attached to the inner gimbal ring. The ultrasonic array is attached to a PCB that is fixedly attached to the outer gimbal ring and the gimbal system comprises a separate motor and micro-gear assembly for each of the inner gimbal ring and the outer gimbal ring. The motors and micro-gear assemblies are configured to tilt the ultrasonic array relative to the base.

In embodiments of the base of the first, third, and fourth aspect of the invention the motor is a step motor configured to generate up to a 45 degrees tilt in variable steps of between 0.1 degrees and 10 degrees in a single step.

All the above and other characteristics and advantages of the invention will be further understood through the following illustrative and non-limitative description of embodiments thereof, with reference to the appended drawings.

BRIEF DESCRIPTION OF THE DRAWINGS

FIG. 4B is the isometric view of FIG. 1 with the outer gimbal ring removed;

FIG. 5 is a bottom view of the gimbal system of the invention;

DETAILED DESCRIPTION OF EMBODIMENTS OF THE INVENTION

Figure 3A:
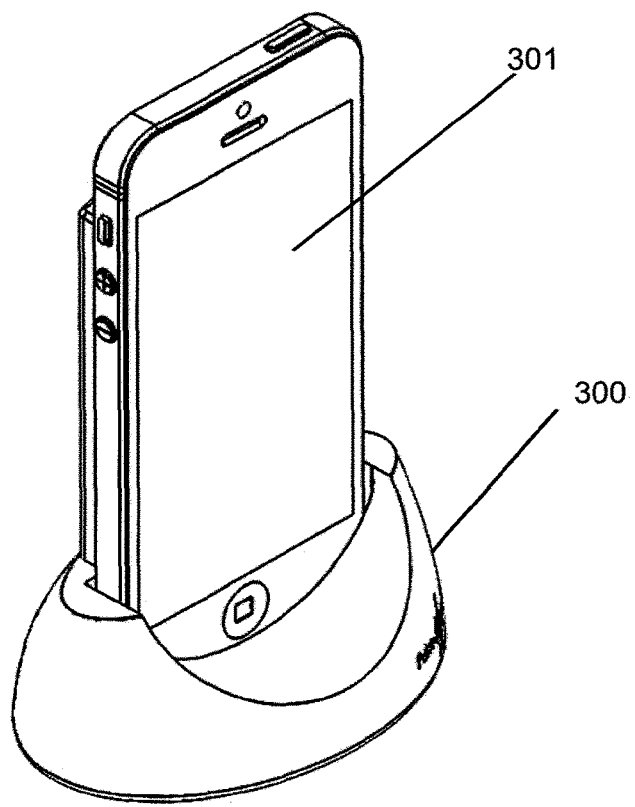
FIG. 3A is a view of the base of FIG. 1 with a smart device connected to it.
Figure 3B:
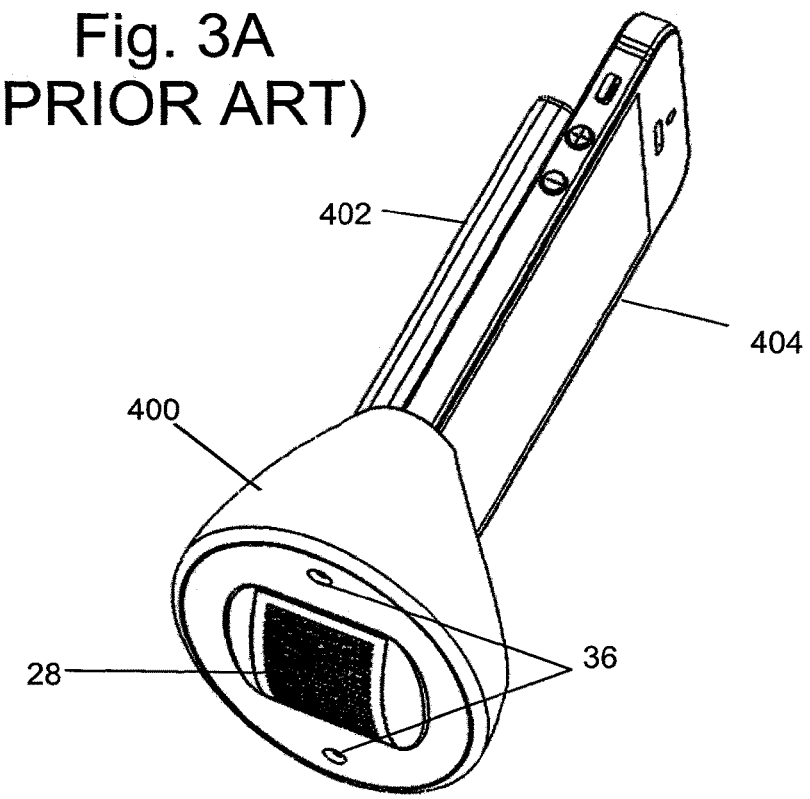
FIG. 3B symbolically shows the ultrasound scanning system of the invention.

FIG. 3B symbolically shows the ultrasound scanning system of the invention. This system is essentially the same as the system described in IL236484 with the additions that are described herein below. Base 400 comprises an integral planar vertical back wall 402 and a cavity into which a smart device 404 can be inserted. At the bottom of base 404 is ultrasound array 28. In the embodiment shown in FIG. 3B, all the capabilities of the smart device 404, e.g. its capacity to receive and to run software and communication capabilities can reside in the base allowing the smart device to be replaced with a display. Shown on the bottom of base 400 are two pressure sensors 36. Pressure sensors 36 are used to measure how much the socket is pushed against the skin. Feedback from the pressure sensors gives a better understanding about the orientation of the base and how much the ultrasound array 28 is pushed against the skin. It is possible to determine the orientation of the ultrasound array from measurements of the pressure against the skin although this method is less accurate then the method described herein below. Embodiments of the base can comprise only one or more than two pressure sensors. In embodiments pressure sensors 36 can be provided on the ultrasound array 28 in addition to or instead of those on the base.

In the prior art ultrasound scanning system of IL236484, the ultrasound array is mounted rigidly within the base 100 so that the transmission/receiving angle of the array is changed by movement of the entire base. The present invention accomplishes its objectives described herein above by interposing a motorized gimbal system between the body of the base and the ultrasound array.

Figure 1:
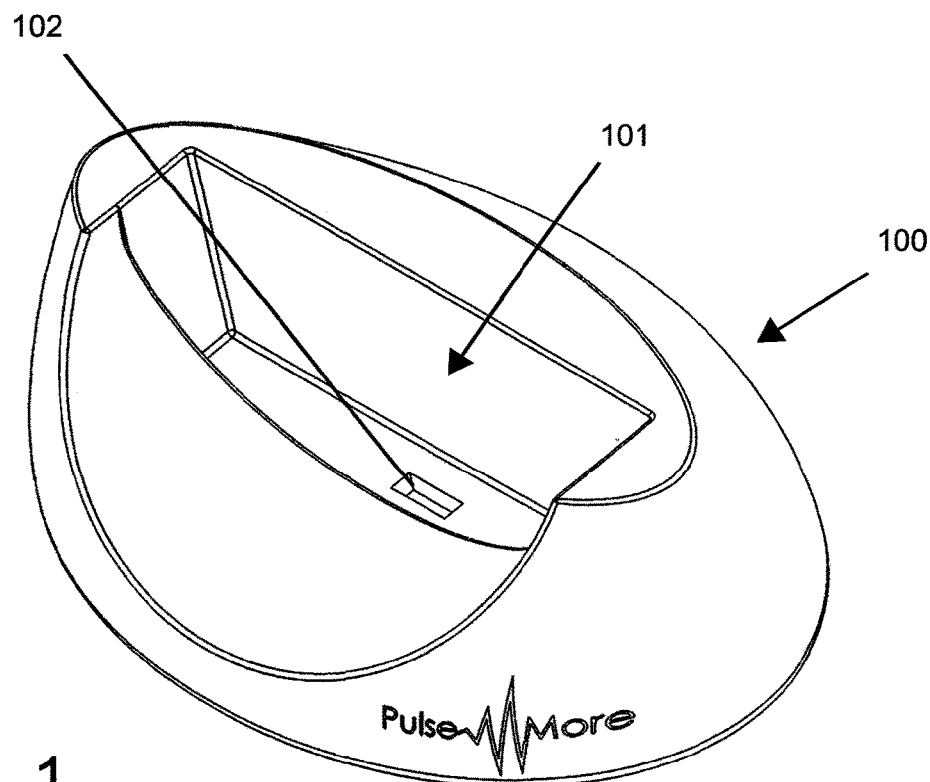
FIG. 1 is a schematic perspective view of a base of a prior art handheld ultrasound scanning system.
Figure 2:
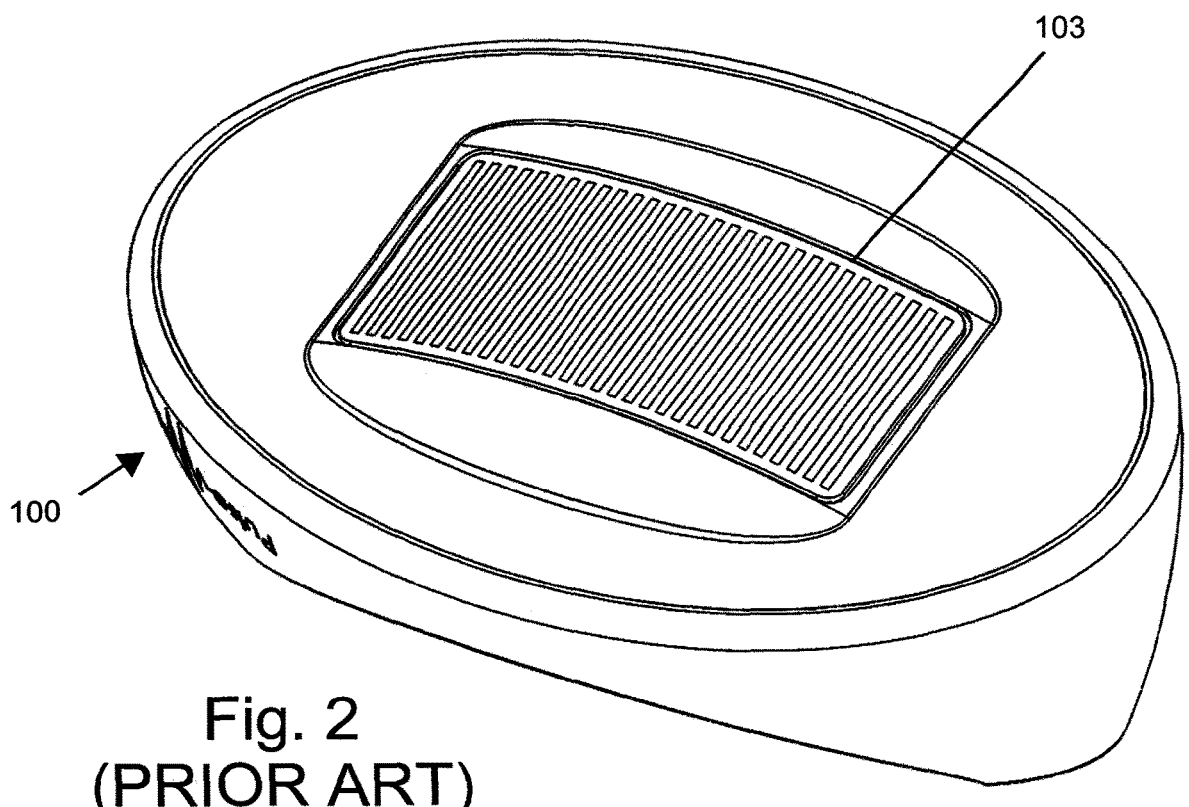
FIG. 2 is a view of the bottom of the base of FIG. 1.
Figure 4A:
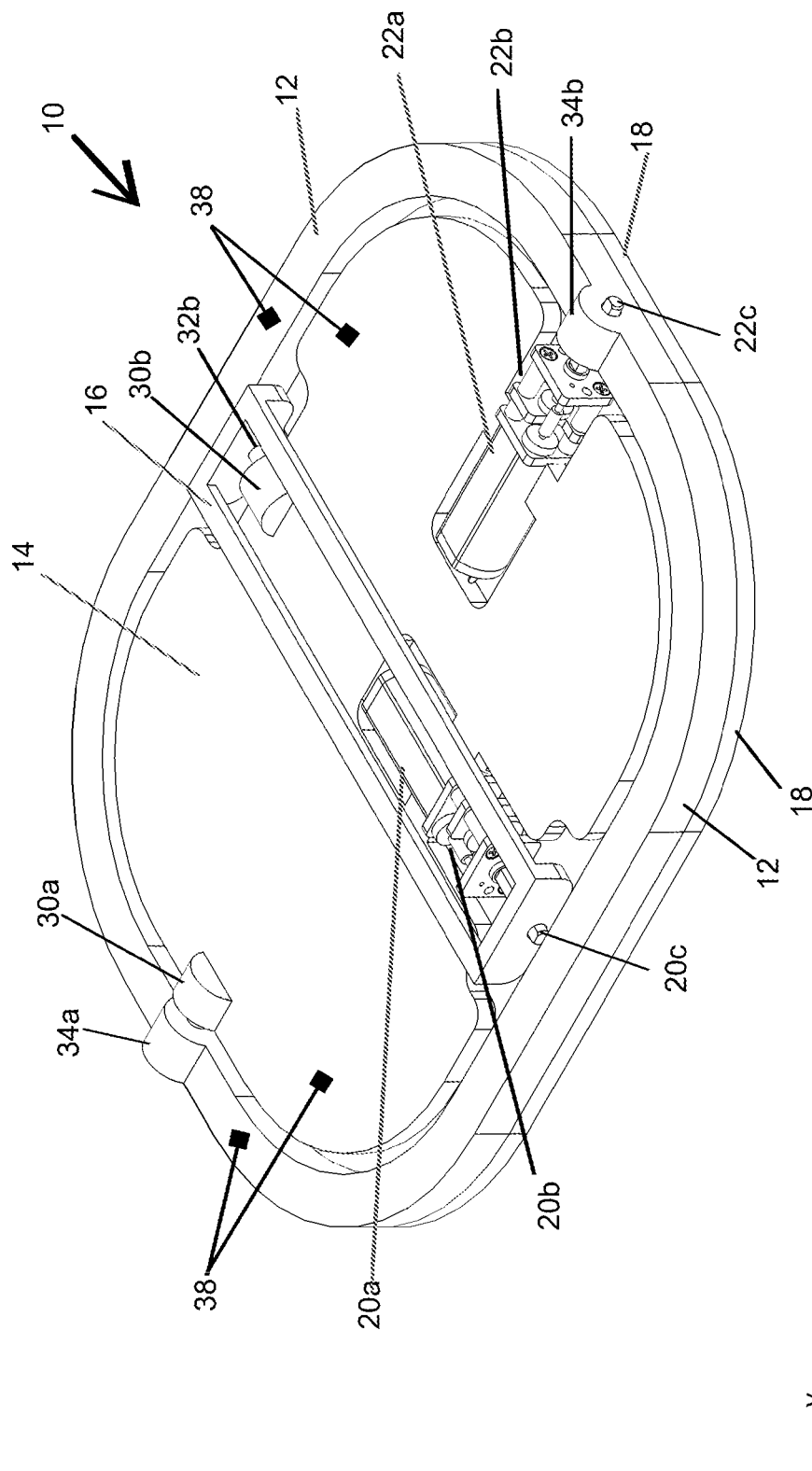
FIG. 4A is an isometric view of an embodiment of the gimbal system of the invention.

FIG. 4A is an isometric view of an embodiment of the gimbal system of the invention. Gimbal system 10 is comprised of an inner gimbal ring 14 and an outer gimbal ring 12. FIG. 4B is the isometric view of FIG. 1 with the outer gimbal ring 12 removed. Gimbal support 16 is rigidly connected to the inside of base 400. The top of gimbal support 16 lies in an x-z plane, which is the reference plane that can be used to see the motion of the gimbal rings in the following figures. PCB 18 to which the ultrasound array (not shown in FIG. 4A or FIG. 4B) is attached is firmly attached to the outer gimbal ring 12.

Gimbal system 10 comprises two micro-gear motor assemblies each comprised of an motor 20a,22a that can be driven in both clockwise and counterclockwise directions and an assembly of micro-gears 20b,22b that transfer power to shafts 20c,22c. Motors 20a,22a can be, for example, electric motors, magnetic motors, or piezo motors.

Motor 20a and micro-gear assembly 20b are fixedly attached to the inner gimbal ring 14. The inner gimbal ring 14 is attached to gimbal support 16 by shaft 20c, which is embedded in gimbal support 16 on one side, and on the other side by pin 32b, which is embedded in block 30b on the inner gimbal ring 14 and can freely turn in a hole in the gimbal support 16. Outer gimbal ring 12 is connected to inner gimbal ring 14 by means of pin 32a, which is embedded in block 30a on the inner gimbal ring and passes into a bore in block 34a on the outer ring. Thus, when motor 20a is activated, the inner gimbal ring 14 and outer gimbal ring 12 are rotated about the z axis in an x-y plane relative to the fixed gimbal support 16.

Motor 22a and micro-gear assembly 22b are fixedly attached to the outer gimbal ring 16. Shaft 22c is embedded in outer gimbal ring 12 on one side of the gimbal ring. On the other side of outer gimbal ring 12 is located pin 32a, which is embedded in block 30a on the inner gimbal ring 14 and can freely turn in a bore in block 34a on outer gimbal ring 12. Thus activating motor 22a causes the outer gimbal ring 12 and attached PCB 18 to rotate around the x axis in a y-z plane relative to the fixed gimbal support 16 and independently of the inner gimbal ring 14.

Shown in the FIG. 4A and in FIG. 4B are 3D accelerometers 38 with digital output that can be read by software on the base or in the smartphone. The accelerometers on the inner gimbal ring 14 and the outer gimbal ring 12 provide information regarding the gimbal movements in order to determine the orientation of the ultrasound array 28 relative to the base. The orientation of the ultrasound array 28 relative to the base can also be known by attaching digital counters to the micro-gear assemblies 20b, 20c or the shafts 20c, 22c. The accelerometers 38 on the ultrasound array PCB 18 measure the velocity and acceleration during movement of the base to insure that the base is not being moved too fast causing smearing of the image. Embodiments of the system can comprise more or less accelerometers 38 then shown in FIGS. 4A and 4B. Accelerometers 38 can also be provided on the base 400 in addition to or instead of on the ultrasound array PCB 18.

FIG. 5 is a bottom view of gimbal system 10 showing the ultrasound array 28 comprising an ultrasonic array with at least one element capable of generating a signal in the range of 1 MHz to 15 MHz. Seen in FIG. 5 are transducer elements 24 and electric contacts 26 that electrically connect transducer elements 24 to an electric circuit on PCB 18.

Figure 6A:
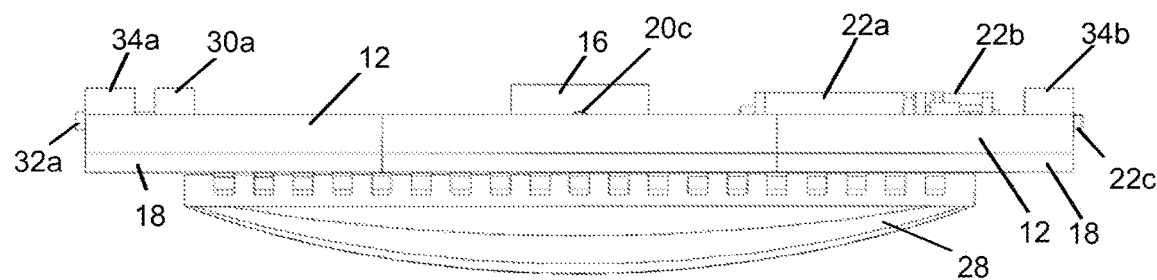
FIG. 6A and FIG. 7A are front views of the gimbal system of the invention showing respectively the gimbal system in its flat position and an angled position.
Figure 7A:
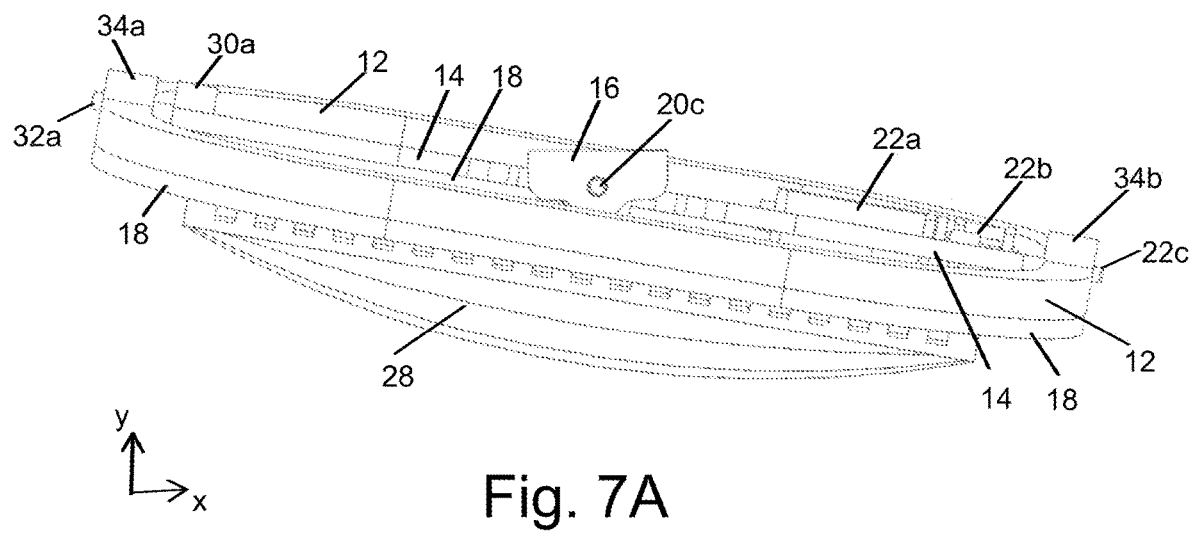
Figure 6B:
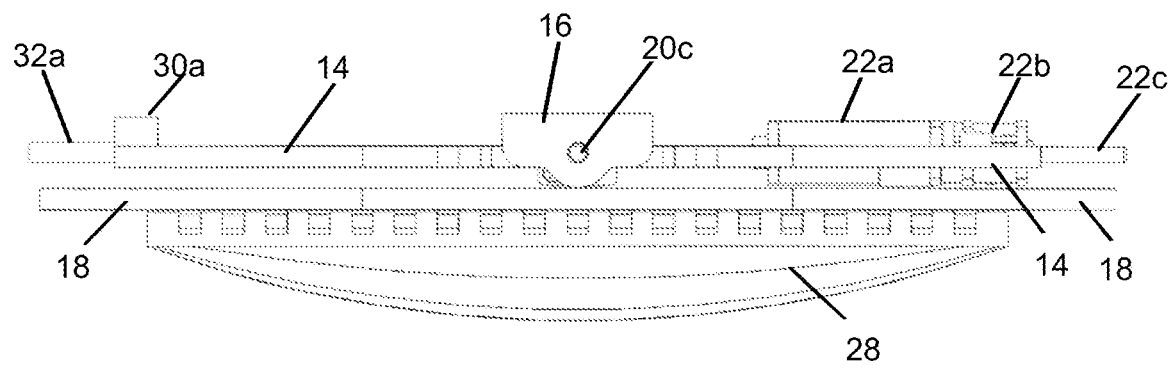
FIG. 6B corresponds to FIG. 6A and FIG. 7B corresponds to FIG. 7A, with the exceptions that the outer gimbal ring has been removed in FIGS. 6B and 7B.

FIG. 6A and FIG. 7A are front views of gimbal system 10 showing respectively the gimbal system in its flat position and an angled position achieved by activating motors 20a, 22b. In this figure, the motors have changed angle by nearly 45 degrees. It is possible to control the angle remotely step by step as desired by use of step motors wherein the steps are, e.g. every 0.1, 0.5, 1, 3, 5, or 10 degrees. FIG. 6B corresponds to FIG. 6A and FIG. 7B corresponds to FIG. 7A, with the exceptions that the outer gimbal ring has been removed in FIGS. 6B and 7B.

In the flat position (FIGS. 6A and 6B), the inner gimbal ring 14 and the outer gimbal ring 12 lie in planes that are parallel to the x-z plane of gimbal support 16. In the angled position the planes in which the inner and outer gimbal rings lie are not parallel to each other or to that of the gimbal support. The angles between the planes are determined by the direction and time for which each of motors 20a and 20b are activated.

Figure 7B:
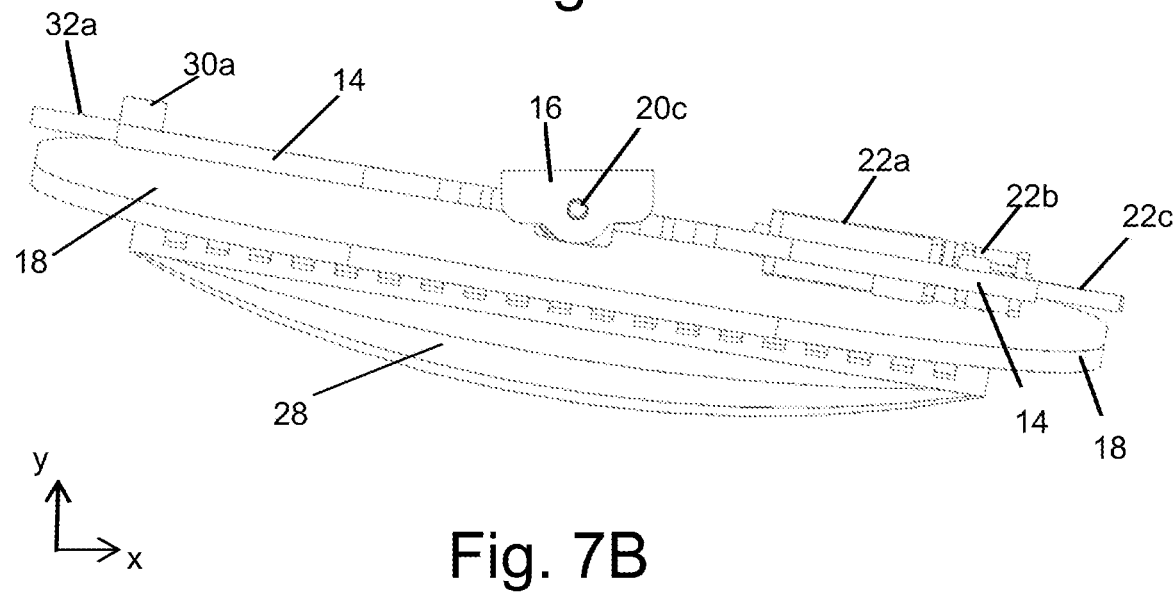

The effect of activating the motors 20a and 22a can best be seen by comparing FIG. 7B to FIG. 6B. In these figures motor 20a has been activated to tip the left side of inner ring 14 and PCB 18 up relative to the right side, effectively forcing the right side of ultrasound array 28 downwards. Motor 22a has been activated to rotate the front edge of PCB 18 downwards relative to the inner gimbal ring 14.

Power for the motors can be supplied from the same source of electrical power used to activate the ultrasonic array with or without a DC to DC converter. Amongst the various options are: a rechargeable battery, sometimes it is possible to use a DC to DC converter that can be located in the base; a rechargeable battery and a switching power supply, comprised of a power stage and a control circuit, located in the base; and a battery in the smart device.

In operation the physician, who can be located thousands of miles away, instructs the patient or an assistant, for example a paramedic, to place the transducer (typically after applying a gel or water) at a certain location on his/her body and to hold it firmly in place. Once this is done the physician takes over remotely controlling the motors of the gimbal system to obtain the images that he requires. If the patient accidently moves the transducer or the physician wants it to be moved to a new location he can direct the patient or paramedic using the two way audio and/or visual communication between the patient's smart device in the base of the ultrasound scanning system and the physician's own smart device.

The control of the gimbal system is accomplished by means of dedicated software located either partially or entirely in the base or smart device of the patient or the physician's smart device or micro/mini-computer. The system can be adapted to allow the physician to use any means known in the art, e.g. a real or virtual joystick or keys on a real or virtual keyboard, for example the four arrow keys for movement in a Cartesian coordinate system, or some other combination of keys to move in another coordinate system, for example, cylindrical or spherical, to provide input to the software to control the motors on the gimbal system.

Another specific example of an application of the current invention is during trauma caused by an accident. Sometimes there is a concern of internal bleeding and appearance of blood around the heart or other vital organs. Common procedure in the emergency room (ER) is for surgeons, emergency physicians, and certain paramedics to carry out a rapid bedside ultrasound examination performed as a screening test for blood around the heart (pericardial effusion) or abdominal organs (hemoperitoneum) after trauma. In the ER, usually there are expensive and large ultrasound machines for carrying out the procedure, which is known as FAST (Focused Assessment with Sonography for Trauma) or eFAST (extended Focused Assessment with Sonography for Trauma). The ultrasound scanning system of the invention can be used by less qualified persons if such a procedure is required during field trauma or in small hospitals or clinics that do not have the expensive ultrasound machines. The video or images can be sent immediately from the handheld system of the invention to expert physicians who can review them, take control of the system by remotely controlling the motors of the gimbal system to which the ultrasound array is attached and to advise the personnel in the field of the next step of treatment during the trauma.

Although embodiments of the invention have been described by way of illustration, it will be understood that the invention may be carried out with many variations, modifications, and adaptations, without exceeding the scope of the claims.

The invention claimed is:

1. A base for an ultrasonic system, the base comprising: elements adapted to connect one of a smart device or a display device to the base such that the base and smart device or the base and the display device can be moved as a single unit, an ultrasonic array with at least one element capable of generating a signal having a frequency in the range between 1 MHz to 15 MHz, and a gimbal system;
wherein the gimbal system is a motorized gimbal system interposed between a body of the base and the ultrasonic array, the motorized gimbal system configured to tilt the ultrasonic array in two dimensions relative to the base, thereby allowing the transmission/reception angle of the array to be changed without moving the base.

2. The base of claim 1, wherein the gimbal system comprises a gimbal support rigidly connected to the inside of the base, an inner gimbal ring rotatably attached to the gimbal support and an outer gimbal ring rotatably attached to the inner gimbal ring wherein the ultrasonic array is attached to a PCB that is fixedly attached to the outer gimbal ring.

3. The base of claim 2, wherein rotation of each of the inner gimbal ring and the outer gimbal ring is caused by a separate motor and micro-gear assembly.

4. The base of claim 3, wherein the motors are activated and controlled from a remote location.

5. The base of claim 4, wherein the motors are activated and controlled by a remotely located real or virtual joystick or by keys on a real or virtual keyboard.

6. The base of claim 3, wherein the motors are chosen from:
electric motors, magnetic motors, and piezo motors.

7. The base according to claim 6, wherein the motor is a step motor configured to generate up to a 45 degrees tilt in variable steps of between 0.1 degrees and 10 degrees in a single step.

8. The base of claim 2, comprising at least one three dimensional accelerometer on at least one of the base, the ultrasound array PCB, the inner gimbal ring, and the outer gimbal ring.

9. The base of claim 1 comprising at least one pressure sensor located on at least one of the base and the ultrasound array.

10. A system for ultrasonic imaging comprising: a base according to claim 1 and one of a smart device or a display device.

11. The system of claim 10, wherein the gimbal system comprises a gimbal support rigidly connected to the inside of the base, an inner gimbal ring rotatably attached to the gimbal support and an outer gimbal ring rotatably attached to the inner gimbal ring wherein the ultrasonic array is attached to a PCB that is fixedly attached to the outer gimbal ring.

12. The system of claim 11, wherein rotation of each of the inner gimbal ring and the outer gimbal ring is caused by a separate motor and micro-gear assembly.

13. The system of claim 12, wherein the motors are activated and controlled from a remote location.

14. The system of claim 13, wherein the motors are activated and controlled by a remotely located real or virtual joystick or by keys on a real or virtual keyboard.

15. The system of claim 12, wherein the motors are chosen from: electric motors, magnetic motors, and piezo motors.

16. The base according to claim 15, wherein the motor is a step motor configured to generate up to a 45 degrees tilt in variable steps of between 0.1 degrees and 10 degrees in a single step.

17. The system of claim 11, comprising at least one 3 dimensional accelerometer on at least one of the base, the ultrasound array PCB, the inner gimbal ring, and the outer gimbal ring.

18. The system of claim 10, comprising at least one pressure sensor located on at least one of the base and the ultrasound array.

19. A base for an ultrasonic system, the base comprising: elements adapted to connect a smart device to the base such that the base and smart device can be moved as a single unit, an ultrasonic array with at least one element capable of generating a signal having frequency in the range between 1 MHz to 15 MHz, and a gimbal system connected to the inside of the base; the gimbal system comprising: an inner gimbal ring rotatably attached to the gimbal support and an outer gimbal ring rotatably attached to the inner gimbal ring wherein the ultrasonic array is attached to a PCB that is fixedly attached to the outer gimbal ring and the gimbal system is configured to tilt the ultrasonic array in two dimensions relative to the base.

20. A base for an ultrasonic system, the base comprising: elements adapted to connect a smart device to the base such that the base and smart device can be moved as a single unit, an ultrasonic array with at least one element capable of generating a signal having frequency in the range between 1 MHz to 15 MHz, and a gimbal system comprised of a gimbal support rigidly connected to the inside of the base, an inner gimbal ring rotatably attached to the gimbal support and an outer gimbal ring rotatably attached to the inner gimbal ring wherein the ultrasonic array is attached to a PCB that is fixedly attached to the outer gimbal ring and the gimbal system comprises a separate motor and micro-gear assembly for each of the inner gimbal ring and the outer gimbal ring, wherein the motors and micro-gear assemblies are configured to tilt the ultrasonic array in two dimensions relative to the base.

21. The base according to claim 20, wherein the motor is a step motor configured to generate up to a 45 degrees tilt in variable steps of between 0.1 degrees and 10 degrees in a single step.

* * * * *